United States Patent [19]

Rodebush et al.

[11] 4,160,659

[45] Jul. 10, 1979

[54] SYNERGISTIC HERBICIDAL COMPOSITIONS

[75] Inventors: James E. Rodebush, Three Forks, Mont.; Gerald H. Thiele, Sunnyvale, Calif.

[73] Assignee: Stauffer Chemical Company, Westport, Conn.

[21] Appl. No.: 890,340

[22] Filed: Mar. 27, 1978

[51] Int. Cl.² .......................... A01N 9/22; A01N 9/28
[52] U.S. Cl. ........................................... 71/95; 71/88
[58] Field of Search ............................................. 71/95

[56] References Cited

U.S. PATENT DOCUMENTS

| 4,069,038 | 1/1978 | Teach ........................................ 71/88 |
| 4,078,495 | 2/1978 | Fates et al. ............................... 71/95 |

Primary Examiner—Catherine L. Mills
Attorney, Agent, or Firm—M. Henry Heines

[57] ABSTRACT

Synergistic herbicidal activity is displayed by compositions comprising the following two components:
(1) 1-allyl-3-chloro-4-chloromethyl-2-pyrrolidone, and
(2) 2-ethoxy-2,3-dihydro-3,3-dimethyl-5-benzofuranyl methanesulfonate.

2 Claims, No Drawings

SYNERGISTIC HERBICIDAL COMPOSITIONS

DESCRIPTION OF THE INVENTION

This invention relates to synergistic herbicidal compositions.

It has been discovered that synergism in the control of undesired vegetation is exhibited by compositions comprising the following two components:

(1) 1-allyl-3-chloro-4-chloromethyl-2-pyrrolidone, which has the structural formula

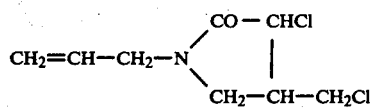

and (2) 2-ethoxy-2,3-dihydro-3,3-dimethyl-5-benzofuranyl methanesulfonate, which has the structural formula

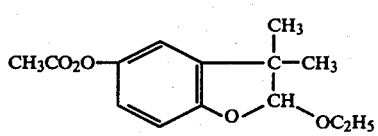

The former compound is a known herbicide, disclosed in U.S. Pat. No. 4,069,038. The latter is also a known herbicide, manufactured by Fisons Corporation under the trade name NORTRON ®.

The term "herbicide", as used herein, means a compound which controls or modifies the growth of plants. By the term "herbicidally effective amount" is meant an amount of compound which causes a modifying effect upon the growth of plants. The terms "plants" and "vegetation" are used herein to include germinant seeds and emerging seedlings as well as established vegetation, including roots and above ground portions. The modifying effects referred to above include all deviations from natural development, for example, killing, retardation, defoliation, desiccation, regulation, stunting, tillering, stimulation, leaf burn, dwarfing and the like.

The term "synergism" is employed in its traditional sense and describes a herbicidal effect of a composition containing two or more active herbicidal compounds which is greater than the sum of the herbicidal effects of the individual compounds when used alone.

The pyrrolidone and sulfonate herbicides are used in a weight ratio of pyrrolidone to sulfonate of 0.001–50:1, preferably 0.01–10:1, and most preferably 0.1–8:1.

The synergistic herbicidal compositions of this invention can be prepared by any conventional method. It is preferred to use herbicidal components in the form of wettable powders or emulsifiable concentrates. Amounts of each component are added to sufficient water to provide the desired rate of application of active ingredient. The compositions of this invention are generally employed at a rate of 0.01 to 50 pounds per acre, preferably 0.1 to 25 pounds per acre. The amount used will depend on the weeds to be controlled and the degree of control desired.

Herbicidal compositions illustrative of those embodied in the instant application were prepared and synergistic effect evaluated in the following examples.

EXAMPLES

The compositions of the present invention were tested for herbicidal activity and synergism by a pre-emergence surface application procedure, conducted as follows:

Fiber flats which were 6 inches wide, 10 inches long, and 2¼ inches deep were filled to a depth of about 2¼ inches with sandy loam soil of moisture content approximately 9%, containing 75 parts per million (ppm) of cis-N[(trichloromethyl)thio]-4-cyclohexene-1,2-dicarboximide (a commercial fungicide) and 50 ppm of 17-17-17 fertilizer (17% N, 17% $P_2O_5$, and 17% $K_2O$ on weight basis). The soil was leveled and a row marker was used to impress eight rows across the width of the flat. In each flat, one row of sugar beets was planted, and one row of each of the following weeds:

TABLE I

| Plant Species Tested | |
|---|---|
| COMMON NAME | SCIENTIFIC NAME |
| pigweed | *Amaranthus retroflexus* |
| mustard | *Brassica juncea* |
| annual morning glory | *Ipomoea purpurea* |
| johnsongrass | *Sorghum halepense* |
| watergrass | *Echinocloa crusgalli* |
| crabgrass | *Digitaria sanguinalis* |
| nutsedge | *Cyperus sp.* |

The flats were then treated by atomizing a measured amount of stock solution evenly over the soil surface. For each compound applied singly, 5 milliliters (ml) of stock solution selected from Table II for the appropriate application rate was used per flat. For compounds applied in combination, a mixture was used consisting of 5 ml each of the appropriate stock solutions selected from the table.

TABLE II

A. 1-Allyl-3-chloro-4-chloromethyl-2-pyrrolidone (71% active ingredient)

| For Application Rate (in pounds per acre): | Quantity (in milligrams) Dissolved in 100 ml Water: |
|---|---|
| ⅛ | 14 |
| ¼ | 28 |
| ½ | 56 |
| 1 | 113 |

B. 2-Ethoxy-2,3-dihydro-3,3-dimethyl-5-benzofuranyl methanesulfonate (95% active ingredient)

| For Application Rate (in pounds per acre): | Quantity (in milligrams) Dissolved in Mixture of 50 ml Acetone & 50 ml Water |
|---|---|
| ¼ | 21 |
| ½ | 42 |
| 1 | 84 |
| 2 | 168 |

Following treatment, the flats were placed in a greenhouse for three weeks and five days at 70°–85° F. where they were watered daily. At the end of this period, the degree of weed control was estimated and recorded as percent control compared to the same species in an untreated check flat of the same age.

The percentage control is based on the total injury to the plants due to all factors including inhibited germination, killing of the plant tissue after emergence, stunting, malformation, chlorosis and other types of injury. The control ratings vary from 0 to 100% where 0 represents no effect with growth equal to the untreated control, and 100 represents complete kill.

Two complete replications were performed of each test. The results of the first are shown in Table III while those of the second are shown in Table IV. The actual results are listed in the columns headed by the symbol "O" (indicating observed result). These results were then compared with the expected results, shown in the columns headed by the symbol "E", derived from Limpel's formula (Limpel et al., 1962, "Weed Control by Dimethylchloroterephthalate Alone and in Certain Combinations," *Proc. NEWCC*, Vol. 16, pp 48–53):

$$E = X + Y - XY/100$$

where

X = observed percent injury when one of the herbicides is used alone, and

Y = observed percent injury when the other herbicide is used alone.

The relationship between the observed result and the expected result for each test is indicated in the columns headed by the symbol "R". When the observed result exceeds the expected result, synergism has been shown, which is represented by the symbol "S". When the observed result is less than the expected result, there is antagonism between the herbicides, represented by the symbol "A". When the observed result equals the expected result, the relationship of the herbicides in the combination is merely additive, as represented by the symbol "Ad."

TABLE III

Test Results in Percent Control - First Replication

| lb/A (1) | lb/A (2) | Pigweed O | E | R | Mustard O | E | R | Annual morning glory O | E | R | Johnsongrass O | E | R | Watergrass O | E | R | Crabgrass O | E | R | Nutsedge O | E | R |
|---|---|---|---|---|---|---|---|---|---|---|---|---|---|---|---|---|---|---|---|---|---|---|
| ¼ | — | 40 | | | 0 | | | 0 | | | 0 | | | 30 | | | 20 | | | 0 | | |
| ½ | — | 60 | | | 0 | | | 0 | | | 0 | | | 100 | | | 50 | | | 0 | | |
| ¾ | — | 90 | | | 20 | | | 10 | | | 20 | | | 100 | | | 90 | | | 30 | | |
| 1 | — | 100 | | | 30 | | | 20 | | | 30 | | | 100 | | | 95 | | | 60 | | |
| — | ¼ | 40 | | | 10 | | | 0 | | | 30 | | | 20 | | | 95 | | | 0 | | |
| — | ½ | 50 | | | 40 | | | 0 | | | 60 | | | 90 | | | 100 | | | 40 | | |
| — | 1 | 85 | | | 80 | | | 30 | | | 100 | | | 100 | | | 100 | | | 98 | | |
| — | 2 | 100 | | | 90 | | | 80 | | | 100 | | | 100 | | | 100 | | | 90 | | |
| ¼ | ¼ | 60 | 64 | A | 0 | 10 | A | 30 | 0 | S | 60 | 30 | S | 90 | 44 | S | 98 | 96 | S | 100 | 0 | S |
| ¼ | ½ | 70 | 70 | Ad | 70 | 40 | S | 70 | 0 | S | 90 | 60 | S | 99 | 93 | S | 100 | 100 | — | 95 | 40 | S |
| ¼ | 1 | 75 | 91 | A | 90 | 80 | S | 75 | 30 | S | 100 | 100 | — | 100 | 10 | — | 100 | 100 | — | 100 | 98 | S |
| ¼ | 2 | 100 | 100 | — | 95 | 90 | S | 80 | 80 | Ad | 100 | 100 | — | 100 | 100 | — | 100 | 100 | — | 100 | 90 | S |
| ½ | ¼ | 60 | 76 | S | 50 | 10 | S | 10 | 0 | S | 80 | 30 | S | 98 | 100 | A | 100 | 98 | S | 40 | 0 | S |
| ½ | ½ | 60 | 80 | A | 60 | 40 | S | 20 | 0 | S | 95 | 60 | S | 100 | 100 | — | 100 | 100 | — | 75 | 40 | S |
| ½ | 1 | 75 | 94 | A | 95 | 80 | S | 95 | 30 | S | 100 | 100 | — | 100 | 100 | — | 100 | 100 | — | 100 | 98 | S |
| ½ | 2 | 100 | 100 | — | 98 | 90 | S | 95 | 80 | S | 100 | 100 | — | 100 | 100 | — | 100 | 100 | — | 100 | 90 | S |
| ¾ | ¼ | 40 | 94 | A | 40 | 28 | S | 20 | 10 | S | 60 | 44 | S | 100 | 100 | — | 100 | 100 | — | 98 | 30 | S |
| ¾ | ½ | 70 | 95 | A | 50 | 52 | A | 30 | 10 | S | 100 | 68 | S | 100 | 100 | — | 100 | 100 | — | 99 | 58 | S |
| ¾ | 1 | 75 | 99 | A | 80 | 84 | A | 80 | 37 | S | 100 | 100 | — | 100 | 100 | — | 100 | 100 | — | 98 | 99 | A |
| ¾ | 2 | 80 | 100 | A | 95 | 92 | S | 95 | 82 | S | 100 | 100 | — | 100 | 100 | — | 100 | 100 | — | 100 | 93 | S |
| 1 | ¼ | 60 | 100 | A | 60 | 37 | S | 60 | 20 | S | 95 | 51 | S | 100 | 100 | — | 100 | 100 | — | 60 | 60 | A |
| 1 | ½ | 70 | 100 | A | 70 | 58 | S | 65 | 20 | S | 100 | 72 | S | 100 | 100 | — | 100 | 100 | — | 100 | 76 | S |
| 1 | 1 | 80 | 100 | A | 95 | 86 | S | 70 | 44 | S | 100 | 100 | — | 100 | 100 | — | 100 | 100 | — | 100 | 99 | S |
| 1 | 2 | 95 | 100 | A | 95 | 93 | S | 98 | 84 | S | 100 | 100 | — | 100 | 100 | — | 100 | 100 | — | 100 | 96 | S |

(1): 1-Allyl-3-chloro-4-chloromethyl-2-pyrrolidone
(2): 2-Ethoxy-2,3-dihydro-3,3-dimethyl-5-benzofuranyl methanesulfonate

TABLE IV

Test Results in Percent Control - Second Replication

| lb/A (1) | lb/A (2) | Pigweed O | E | R | Mustard O | E | R | Annual morning glory O | E | R | Johnsongrass O | E | R | Watergrass O | E | R | Crabgrass O | E | R | Nutsedge O | E | R |
|---|---|---|---|---|---|---|---|---|---|---|---|---|---|---|---|---|---|---|---|---|---|---|
| ¼ | — | 50 | | | 0 | | | 0 | | | 0 | | | 30 | | | 0 | | | 0 | | | | |
| ½ | — | 60 | | | 0 | | | 0 | | | 0 | | | 95 | | | 80 | | | 0 | | | | |
| ¾ | — | 65 | | | 0 | | | 20 | | | 0 | | | 100 | | | 100 | | | 50 | | | | |
| 1 | — | 70 | | | 30 | | | 30 | | | 50 | | | 100 | | | 100 | | | 70 | | | | |
| — | ¼ | 60 | | | 20 | | | 10 | | | 40 | | | 30 | | | 95 | | | 0 | | | | |
| — | ½ | 65 | | | 40 | | | 10 | | | 80 | | | 100 | | | 100 | | | 40 | | | | |
| — | 1 | 70 | | | 90 | | | 10 | | | 100 | | | 100 | | | 100 | | | 70 | | | | |
| — | 2 | 80 | | | 95 | | | 60 | | | 100 | | | 100 | | | 100 | | | 98 | | | | |
| ¼ | ¼ | 60 | 80 | A | 20 | 20 | Ad | 10 | 10 | Ad | 20 | 40 | A | 90 | 51 | S | 98 | 95 | S | 0 | 0 | Ad |
| ¼ | ½ | 70 | 83 | A | 40 | 40 | Ad | 30 | 10 | S | 100 | 80 | S | 95 | 100 | A | 100 | 100 | — | 40 | 40 | Ad |
| ¼ | 1 | 75 | 85 | A | 70 | 90 | A | 60 | 10 | S | 100 | 100 | — | 100 | 100 | — | 100 | 100 | — | 70 | 70 | Ad |
| ¼ | 2 | 95 | 90 | S | 98 | 95 | S | 90 | 60 | S | 100 | 100 | — | 100 | 100 | — | 100 | 100 | — | 98 | 98 | Ad |
| ½ | ¼ | 90 | 84 | S | 80 | 20 | S | 50 | 10 | S | 60 | 40 | S | 100 | 97 | S | 95 | 99 | A | 80 | 0 | S |
| ½ | ½ | 95 | 86 | S | 90 | 40 | S | 80 | 10 | S | 100 | 80 | S | 100 | 100 | — | 100 | 100 | — | 95 | 40 | S |
| ½ | 1 | 98 | 88 | S | 95 | 90 | S | 80 | 10 | S | 100 | 100 | — | 100 | 100 | — | 100 | 100 | — | 95 | 70 | S |
| ½ | 2 | 100 | 92 | S | 95 | 95 | Ad | 95 | 60 | S | 100 | 100 | — | 100 | 100 | — | 100 | 100 | — | 98 | 98 | Ad |
| ¾ | ¼ | 90 | 86 | S | 70 | 20 | S | 30 | 28 | S | 60 | 40 | S | 100 | 100 | — | 100 | 100 | — | 80 | 50 | S |
| ¾ | ½ | 95 | 88 | S | 80 | 40 | S | 50 | 28 | S | 100 | 80 | S | 100 | 100 | — | 100 | 100 | — | 95 | 70 | S |
| ¾ | 1 | 98 | 90 | S | 95 | 90 | S | 70 | 28 | S | 100 | 100 | — | 100 | 100 | — | 100 | 100 | — | 98 | 85 | S |
| ¾ | 2 | 100 | 93 | S | 100 | 95 | S | 98 | 68 | S | 100 | 100 | — | 100 | 100 | — | 100 | 100 | — | 95 | 99 | A |
| 1 | ¼ | 80 | 88 | A | 50 | 44 | S | 20 | 37 | A | 70 | 70 | Ad | 100 | 100 | — | 100 | 100 | — | 90 | 70 | S |
| 1 | ½ | 85 | 90 | A | 60 | 58 | S | 60 | 37 | S | 85 | 90 | A | 100 | 100 | — | 100 | 100 | — | 90 | 82 | S |
| 1 | 1 | 90 | 91 | A | 100 | 93 | S | 90 | 37 | S | 90 | 100 | A | 100 | 100 | — | 100 | 100 | — | 95 | 91 | S |

TABLE IV-continued

| | | | | | | | | | Annual | | | | | | | | | | | | |
|---|---|---|---|---|---|---|---|---|---|---|---|---|---|---|---|---|---|---|---|---|---|
| lb/A | lb/A | Pigweed | | | Mustard | | | morning glory | | | Johnsongrass | | Watergrass | | Crabgrass | | Nutsedge | | | | | |
| (1) | (2) | O | E | R | O | E | R | O | E | R | O | E | R | O | E | R | O | E | R | O | E | R |
| 1 | 2 | 95 | 94 | S | 100 | 97 | S | 98 | 72 | S | 100 | 100 | — | 100 | 100 | — | 100 | 100 | — | 95 | 99 | A |

(1): 1-Allyl-3-chloro-4-chloromethyl-2-pyrrolidone
(2): 2-Ethoxy-2,3-dihydro-3,3-dimethyl-5-benzofuranyl methanesulfonate The compositions of the present invention are useful as herbicides in controlling the growth of undesirable vegetation by pre-plant or post-plant incorporation, or pre-emergence or post-emergence application to the locus where control is desired. The compositions are generally embodied in formulations suitable for convenient application. In general, such formulations will contain inert or occasionally active ingredients or diluent carriers in addition to the active compound. Examples of such ingredients or carriers are water, organic solvents, dust carriers, granular carriers, surface active agents, oil and water, water in oil emulsions, wetting agents, dispersing agents, and emulsifying agents. The herbicidal formulations generally take the form of dusts, wettable powders, granules, solutions, or emulsifiable concentrates.

Dusts are free-flowing powder compositions containing the herbicidal compound impregnated on a particulate carrier. The particle size of the carrier is usually in the range of from about 30 to 50 microns. Examples of suitable carriers are talc, bentonite, diatomaceous earth, and pyrophyllite. Anticaking and antistatic agents can be added if desired. The composition generally contains up to 50% of active ingredient.

Wettable powders are finely divided compositions comprising a particulate carrier impregnated with the herbicidal compound and additionally containing one or more surface active agents. The surface active agent promotes rapid dispersion of the powder in aqueous medium to form stable, sprayable suspensions. A wide variety of surface active agents can be used, for example, long chain fatty alcohols and alkali metal salts of the sulfated fatty alcohols; salts of sulfonic acid; esters of long chain fatty acids; and polyhydric alcohols, in which the alcohol groups are free, omega-substituted polyethylene glycols of relatively long chain length. A list of surface active agents suitable for use in agriculture formulations can be found in Pesticide Formulations by Wade Van Valkenburg, Marcel Dekker, Inc. New York 1973 at pages 79–84.

Granules comprise the herbicidal composition impregnated on a particulate inert carrier having a particle size of about 1 to 2 millimeters in diameter. The granules can be made by spraying a solution of the active ingredient in a volatile solvent onto the granular carrier. Suitable carriers in preparation of granules include clay, vermiculite, sawdust, granular carbon, and the like.

The herbicidal compositions can also be applied to the soil in the form of a solution in a suitable solvent. Solvents frequently used in herbicidal formulations include kerosene, fuel oil, xylene, petroleum fractions with boiling ranges above xylene, and aromatic petroleum fractions rich in methylated naphthalenes.

Emulsifiable concentrates consist of an oil solution of the herbicide along with an emulsifying agent. Prior to use the concentrate is diluted with water to form a suspended emulsion of oil droplets. The emulsifiers used are usually a mixture of anionic and nonionic surfactants. Other additives such as spreading agents and stickers can be included in the emulsifiable concentrate.

The formulations described above, employing phytotoxic or herbicidally effective amounts of the compositions described herein, are applied to the loci where control is desired in any conventional manner. The loci referred to above include soil, seeds, seedlings, and the actual plants. Dusts and liquid compositions can be applied by the use of powder dusters, boom and hand sprayers and spray dusters. The compositions can also be applied from airplanes as dusts or sprays because they are effective in very low dosages. In order to modify or control growth of germinating seeds or emerging seedlings, as a typical example, the dust and liquid compositions are applied to the soil according to conventional methods and are distributed in the soil to a depth of at least one-half inch below the soil surface. It is not necessary that the phytotoxic compositions be admixed with the soil particles. Instead, these compositions can be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations.

The phytotoxic compositions of this invention can also contain other additaments, for example, fertilizers, pesticides and the like, used as adjuvants or in combination with any of the above-described adjuvants. Other phytotoxic compounds useful in combination with the above-described compositions include, for example, 2,4-dichlorophenoxyacetic acids, 2,4,5-trichlorophenoxyacetic acid, 2-methyl-4-chlorophenoxyacetic acid, and the salts, esters and amides thereof; triazine derivatives, such as 2,4-bis(3-methoxypropylamino)-6-methyl-thio-s-triazine; 2-chloro-4-ethylamino-6-isopropylamino-s-triazine, and 2-ethyl-amino-4-isopropylamino-6-methylmercapto-s-triazine; urea derivatives such as 3-(3,4-dichlorophenyl)-1,1-dimethyl urea, and acetamides such as N,N-diallyl-α-chloroacetamide, N-(α-chloroacetyl) hexamethyleneimine, and N,N-diethyl-α-bromoacetamide, and the like; benzoic acids such as 3-amino-2,5-dichlorobenzoic; S-ethyldipropylthiocarbamate; S-ethyl hexahydro-1H-azepine-1-carbothioate and the like. Fertilizers useful in combination with the active ingredients include, for example, ammonium nitrate, urea and superphosphate. Other useful additaments include materials in which plant organisms take root and grow, such as compost, manure, humus, sand and the like.

The amount of a composition of the present invention which constitutes a phytotoxic or herbicidally effective amount depends upon the nature of the seeds or plants to be controlled. The rate of application of active ingredient varies from about 0.01 to about 50 pounds per acre, preferably about 0.1 to about 25 pounds per acre with the actual amount used depending on the overall cost and the desired results. It will be readily apparent to one skilled in the art that compositions exhibiting lower herbicidal activity will require a higher dosage rate for the same degree of control than more active compounds.

What is claimed is:

1. A synergistic herbicidal composition consisting essentially of a mixture of
   (1) a herbicidally effective amount of 1-allyl-3-chloro-4-chloromethyl-2-pyrrolidone and
   (2) a herbicidally effective amount of 2-ethoxy-2,3-dihydro-3,3-dimethyl-5-benzofuranyl methanesulfonate, in a weight ratio of (1) to (2) of 0.1–8:1.

2. A method of controlling undesirable vegetation which comprises applying to the locus where control is desired a synergistic herbicidal composition consisting essentially of a mixture of
   (1) a herbicidally effective amount of 1-allyl-3-chloro-4-chloromethyl-2-pyrrolidone and
   (2) a herbicidally effective amount of 2-ethoxy-2,3-dihydro-3,3-dimethyl-5-benzofuranyl methanesulfonate, in a weight ratio of (1) to (2) of 0.1–8:1.